United States Patent [19]

Sarantakis

[11] 4,143,032
[45] Mar. 6, 1979

[54] HEXAPEPTIDES HAVING ANALGESIC ACTIVITIES

[75] Inventor: Dimitrois Sarantakis, West Chester, Pa.

[73] Assignee: American Home Products Corporation, New York, N.Y.

[21] Appl. No.: 807,865

[22] Filed: Jun. 20, 1977

[51] Int. Cl.² .................. C07C 103/52; A61K 37/00
[52] U.S. Cl. ........................... 260/112.5 R; 424/177
[58] Field of Search ............... 260/112.5 R; 424/177

[56] References Cited

PUBLICATIONS

Pert. et al., "Life Science" 18, 1976 pp. 1473–1482.
A. J. Kastin et al., Brain Research Bulletin, 1, 1976 pp. 583–589.
L. Terenius et al., Biochem. and Biophys. Res. Comm. 71, 1976 pp. 175–179.
Belluzzi, Nature 262, 1976 pp. 738–739.
C. Pert. et al., Science 194, 1976 pp. 330–332.
D. H. Coy et al., Biochem. and Biophys. Res. Comm. 73, 1976 pp. 632–638.
Kastin et al., Pharm. Biochem. & Behavior 5, 1976 pp. 691–695.
C. Pert et al., Opiates and Endogenous Opioid Peptides 1976 pp. 79–86.

*Primary Examiner*—Delbert R. Phillips
*Attorney, Agent, or Firm*—Richard K. Jackson

[57] ABSTRACT

Hexapeptides of the formula:

H-Arg-Tyr-X-Gly-Phe-Y-Z wherein X is D-Ala, D-Met, D-Leu, D-Pro, D-His, D-Trp or D-Phe; Y is D-Leu, D-Met, D-Pro or D-Lys; and Z is --OH, —NH$_2$, or —NHC$_2$H$_{2n+1}$ where n is 1, 2, 3, or 4 or a pharmaceutically acceptable salt thereof, exert an analgesic effect in warm-blooded animals upon intravenous administration.

1 Claim, No Drawings

HEXAPEPTIDES HAVING ANALGESIC ACTIVITIES

BACKGROUND OF THE INVENTION

Enkephalin, a natural opiate receptor agonist in the brain, has been identified [see Hughes et al., Nature, 258, 577 (1975)] as a mixture of two pentapeptides: H-Tyr-Gly-Gly-Phe-Met-OH (methionine-enkephalin) and H-Tyr-Gly-Gly-Phe-Leu-OH (leucineenkephalin). Both peptides mimic the ability of morphine to block electrically evoked contractions of mouse vas deferens and guinea pig ileum, and both inhibit the stereospecific receptor binding of the opiate antagonist 3H-naloxone in brain homogenates. It has been reported that methionine-enkephalin and leucine-enkephalin, when administered by injection in the brain ventricle in rats, induce a profound analgesia that is fully reversible by naloxone. [See Beluzzi et al., Nature, 260, 625 (1976)]. The enkephalins are inactive peripherally, however, and it is believed that the enkephalins are rapidly destroyed by blood enzymes and/or are poorly transported across the blood-brain barrier.

Various structural variations of methionine-enkephalin and leucine-enkephalin are described in the literature. For example, the pentapeptide H-Tyr-Gly-Gly-Phe-Thr-OH, wherein the fifth amino acid residue (methionine or leucine) is replaced by threonine, is described by Chang et al., Life Sciences, 18, 1473 (1976). Similarly, a long acting synthetic pentapeptide, Tyr-D-Ala-Gly-Phe-Met amide is described in Pert et al., Science, 194, 330 (1976); like the natural enkephalins, it is inactive peripherally, for example upon intravenous administration. In addition, Baxter et al., British Journal of Pharmacology, March 2, 1977, pages 455P-456P and 523P report activity in the compound Tyr-D-Ala-Gly-Phe-D-Leu when administered intracerebroventricularly.

The present invention concerns novel synthetic hexapeptides which are able to produce an analgesic effect in warm-blooded animals upon peripheral administration.

Description of the Invention

The invention sought to be patented resides in the concept of a chemical compound of the formula:

Arg-Tyr-X-Gly-Phe-Y-Z     (I)

wherein X is D-Ala, D-Met, D-Leu, D-Pro, D-His, D-Trp, or D-Phe; Y is D-Leu, D-Met, D-Pro, or D-Lys; and Z is —OH, $NH_2$, $-NHC_2H_{2n+1}$, where n is 1, 2, 3, or 4, or a pharmaceutically acceptable salt.

The tangible embodiments of the invention have the inherent applied use characteristic of exerting analgesic effects in warm-blooded animals as evidenced by standard test procedures.

The compounds of the invention are prepared by typical solid phase procedures on a supporting resin. The hexapeptide is cleaved from the resin with HF, and purified by partition chromatography on Sephadex G-25 using the system butanol-acetic acid-water (BAW), 4-1-5.

In the case of the pharmaceutically acceptable salts of the invention, there is contemplated addition salts of the hexapeptides with non-toxic, pharmaceutically acceptable acids. Suitable acids, both organic and inorganic, will be readily apparent to those skilled in the art, for example: hydrochloric, phosphoric, maleic, acetic, citric, succinic, malic, and the like. Likewise, salts of the free hexapeptidic acid which are embraced by the expression "pharmaceutically acceptable salts", include the sodium, potassium, and ammonium salts. The salts are prepared and isolated by conventional methods from the corresponding hexapeptides.

The symbols used for representing the amino acid residues in Formula I and in the other formulae employed herein are defined according to the IUPAC-IUB Commission on Biochemical Nomenclature Recommendations (1971), Archives of Biochemistry and Biophysics, 150, 1–8 (1972). All chiral amino acid residues identified without prefix in this specification and in the claims are in the natural or L-configuration. Amino acid residues preceded with the prefix "D-" are in the D, or "unnatural" configuration.

The analgesic activity of the compounds of the invention can be demonstrated in rats using the rat-tail flick method of D'Amour and Smith, J. Pharmacol. Exp., Therap., 72, 74 (1941). In this procedure, a single intravenous dose of from 0.5 to 20 mg/kg., will produce analgesia in the rat. Preferably, a dose of from 1 to 10 mg/kg. is employed. The exact dose to be employed will vary depending on the particular compound employed and the degree of analgesia desired. The determination of the precise dose to produce the desired effect will be readily ascertained by those skilled in the art. With representative compound H-Arg-Tyr-D-Ala-Gly-Phe-D-Leu-$NH_2$, the following results were obtained:

| Dose | No. Showing Analgesic/No. Tested |
|---|---|
| 5 mg/kg. i.v. | 6/6 |
| 2.5 mg/kg. i.v. | 2/6 |
| 1.0 mg/kg. i.v. | 2/6 |

The following examples more specifically set forth the method of synthesis of the compounds of the invention.

Example 1 tert-Butyloxycarbonyl-$N^g$-Tosyl-L-Arginyl-O-Benzyl-L-Tyrosyl-D-Alanyl-Glycyl-L-Phenylalanyl-D-Leucyl-Benzhydrylamine Polystyrene Eight grams of benzhydrylamine polystyrene resin (Beckman) (Substitution 0.4 m moles/g.) which had been neutralized with 12 percent triethylamine in DMF was treated in a solid phase reactor with 4 grams t-Boc-D-Leucine and 18 ml. of 1M DIC in DMF for four hours at room temperature. The resin was then washed in the reactor in accordance with steps 11 and 12 of the following Schedule A. The ninhydrin test was negative. Boc-Phe-OH, Boc-Gly-OH, Boc-D-Ala-OH, Boc-Tyr(Bzl)-OH and Boc-Arg(Tos)-OH were then incorporated individually in accordance with Schedule A to obtain the title peptidoresin.

Schedule A
1. Wash with $CH_2Cl_2 \times 3$
2. Treat with TFA-$CH_2Cl_2$-EDT (1:1:5%, v/v) for 5 min.
3. Treat as in 2 for 25 min.
4. Wash with $CH_2Cl_2 \times 3$
5. Wash with DMF
6. Treat with 12% TEA in DMF twice for 3 min.
7. Wash with DMF 8. Wash with CH$_2$Cl$_2$ × 3
9. Treat with 4 equivalents of the corresponding amino acid derivative in CH$_2$Cl$_2$—DMF and stir for 5 min.
10. Add in two portions 5 equivalents of DIC dissolved in CH$_2$Cl$_2$ and over a period of 30 min. Reaction time 6 hours.
11. Wash with DMF × 3
12. Wash with CH$_2$Cl$_2$ × 3
13. Test ninhydrin reaction according to Kaiser et al., Annal. Biochem., 34, 595 (1970). In case of incomplete reaction repeat lines 9 to 13 as above.

Example 2

L-Arginyl-L-Tyrosyl-D-Alanyl-Glycyl-L-Phenylalanyl-D-Leucyl Amide Diacetate

The peptidoresin of the previous example was mixed with anisole (20 ml.) and treated with liquid anhydrous HF (200 mg.) for 45 minutes at 15° C. The excess HF was removed under vacuo and the residue was taken in 5% aqueous AcOH and filtered. The filtrate was treated with anion exchange resin Bio Rad AG 3 (acetate form) and filtered. The filtrate was lyophilyzed to afford a solid. This crude material was applied onto a column of Sephadex G 15 (2.5 × 120 cm.) and eluted with 10% aqueous AcOH. Fractions of 5.5 ml. were collected and the material which emerged in fractions 77–94 was pooled and lyophilyzed to afford the title hexapeptide amide.

TLC, Avicel precoated plates, R$_f$(BWA, 4:1:1, v/v) 0.61 R$_f$(tAWP, 7:6:7, v/v) 0.69.

Amino acid analysis: Gly(1)1, Ala(1)1, Leu(1)1, Tyr(1)1, Phe(1)1, Arg(1)1, NH$_3$(1)1.08.

Example 3 tert-Butyloxycarbonyl-N$^g$-Tosyl-L-Arginyl-O-Benzyl-L-Tyrosyl-D-Alanyl-Glycyl-L-Phenylalanyl-D-Leucyl Hydroxymethyl Polystrene Ester Chloromethylated polystrene resin (8 g.) is esterified with Boc-D-Leu-OH (1.7 g.) according to Gisin, Helv. Chim. Acta., 56, 1976 (1973) and the polymeric ester is treated according to Schedule A of Example 1 for the incorporation of Boc-Phe-OH, Boc-Gly-OH, Boc-D-Ala-OH, Boc-Tyr(Bzl)-OH, and Boc-Arg(Tos)-OH to obtain the title peptidoresin.

Example 4

L-Arginyl-L-Tyrosyl-D-Alanyl-Glycyl-L-Phenylalanyl-D-Leucyl-OH

The peptidoresin of the previous example was treated as in Example 2 to afford the title hexapeptide.

Example 5 tert-Butyloxycarbonyl-N$^g$-Tosyl-L-Arginyl-O-Benzyl-L-Tyrosyl-D-Alanyl-Glycyl-L-Phenylalanyl-D-Leucyl-Ethylamide The peptidoresin of Example 3 is treated with ethylamine in a sealed flask for 10 hours then the excess ethylamine is evaporated off and the residue is extracted with DMF and filtered. The filtrate is evaporated to dryness and the residue is triturated with water to give the title hexapeptide amide.

Example 6

L-Arginyl-L-Tyrsoyl-D-Alanyl-Glycyl-L-Phenylalanyl-D-Leucyl-Ethylamide

The protected hexapeptide ethylamide is treated with liquid HF in the presence of anisole as in Example 2 to afford the title compound.

What is claimed is:
1. The compound L-arginyl-L-tyrosyl-D-alanylglycyl-L-phenylalanyl-D-leucyl amide or a pharmaceutically acceptable salt thereof.

* * * * *